(12) United States Patent
Blanke et al.

(10) Patent No.: US 10,349,899 B2
(45) Date of Patent: Jul. 16, 2019

(54) SYSTEM AND METHOD FOR PREDICTING HALLUCINATIONS

(71) Applicant: ECOLE POLYTECHNIQUE FEDERALE DE LAUSANNE (EPFL), Lausanne (CH)

(72) Inventors: Olaf Blanke, Nyon (CH); Giulio Rognini, Genève (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/813,184

(22) Filed: Nov. 15, 2017

(65) Prior Publication Data

US 2018/0177462 A1  Jun. 28, 2018

(30) Foreign Application Priority Data

Dec. 23, 2016  (EP) .................................... 16206649

(51) Int. Cl.
*A61B 5/00* (2006.01)
*B25J 3/04* (2006.01)
(Continued)

(52) U.S. Cl.
CPC .......... *A61B 5/7275* (2013.01); *A61B 5/4005* (2013.01); *A61B 5/4064* (2013.01); *A61B 5/4082* (2013.01); *A61N 1/36082* (2013.01); *B25J 3/04* (2013.01); *B25J 13/025* (2013.01); *A61B 5/16* (2013.01); *B25J 9/1689* (2013.01)

(58) Field of Classification Search
CPC combination set(s) only.
See application file for complete search history.

(56) References Cited

U.S. PATENT DOCUMENTS

| | | | |
|---|---|---|---|
| 6,123,661 A | 9/2000 | Suzuki et al. | |
| 6,585,668 B2 | 7/2003 | Nissim | |
| 2016/0176053 A1* | 6/2016 | Rognini | ............. A61N 1/36082 700/248 |

OTHER PUBLICATIONS

Gilles et al., Feeling of Presence in Parkinson's Disease, Journal of Neurology, Neurosurgery, and Psychiatry; May 7, 2011; 2011: 82, pp. 1219-1224 (Year: 2011).*

(Continued)

*Primary Examiner* — Nabil H Syed
*Assistant Examiner* — Cal J Eustaquio
(74) *Attorney, Agent, or Firm* — Andre Roland S.A.; Nikolaus Schibli

(57) ABSTRACT

A system for predicting a likelihood of an occurrence of hallucinations in a subject including a master device configured to be at least one of moved, moved on, and manipulated by a subject, a slave device operably connected with the master device and adapted so that the subject is directly or indirectly touched by the slave device according with the master device's movement, a computer device operably connected to both the master and the slave device, the computer device configured to modulate at least one of a time, space, and force activation of the slave device in response to an activation of the master device, record data regarding a difference in at least one of time, space and force activation, compare the recorded data with reference data, and graphically or numerically showing the result of the comparison on a display device, as an indicator of the likelihood of the occurrence of hallucinations in a subject.

21 Claims, 4 Drawing Sheets

(51) Int. Cl.
  A61N 1/36    (2006.01)
  B25J 13/02   (2006.01)
  A61B 5/16    (2006.01)
  B25J 9/16    (2006.01)

(56) References Cited

OTHER PUBLICATIONS

European Search Report of EP16206649.2 dated Jun. 26, 2017.
G. Rognini et al. "Visuo-tactile integration and body ownership during self-generated action" European Journal of Neuroscience, vol. 37 pp. 1120-1129, 2013.
M. Hara et al. "A Novel Approach to the Manipulation of Body-Parts Ownership Using a Bilateral Master-Slave System", 2011 IEEE/RSJ International Conference on Intelligent Robots and Systems Sep. 25-30, 2011, pp. 4664-4669.
Non-Final Rejection dated Oct. 18, 2017 of U.S. Appl. No. 14/973,834.
Preliminary Opinion of the European Search Authority dated Jun. 26, 2017.
Urwyler, P., Nef, T., Killen, A., Collerton, D., Thomas, A., Burn, D., . . . & Mosimann, U. P. (2014). Visual complaints and visual hallucinations in Parkinson's disease. Parkinsonism & related disorders, 20(3), 318-322.
Blanke et al., "Neurological and robot-controlled induction of an apparition," Current Biology, vol. 24, 2014, supplemental information.
Blanke et al., "Neurological and robot-controlled induction of an apparition," Current Biology, vol. 24, pp. 2681-2686, 2014.
Jalenques et al. "Valence émotionnelle des mots dans la schizophrénie," L'Encéphale, vol. 39, pp. 189-197, 2013.
Agid, Y. (1991). Parkinson's disease: pathophysiology. The Lancet, 337(8753), 1321-1324.
Baker, W. L., Silver, D., White, C. M., Kluger, J., Aberle, J., Patel, A. A., & Coleman, C. I. (2009). Dopamine agonists in the treatment of early Parkinson's disease: a meta-analysis. Parkinsonism & related disorders, 15(4), 287-294.
Diederich, N. J., Fénelon, G., Stebbins, G., & Goetz, C. G. (2009). Hallucinations in Parkinson disease. Nature Reviews Neurology, 5(6), 331-342.
Ravina, B., Marder, K., Fernandez, H. H., Friedman, J. H., McDonald, W., Murphy, D., . . . & Factor, S. (2007). Diagnostic criteria for psychosis in Parkinson's disease: report of an NINDS, NIMH work group. Movement Disorders, 22(8), 1061-1068.
Wood, R. A., Hopkins, S.A., Moodley, K. K., & Chan, D. (2015). Fifty percent prevalence of extracampine hallucinations in Parkinson's disease patients. Frontiers in neurology, 6.
Final Office Action for U.S. Appl. No. 14/973,834 dated Feb. 23, 2018.
Non-final Office Action for U.S. Appl. No. 14/973,834 dated Oct. 18, 2017.

\* cited by examiner

SYSTEM AND METHOD FOR PREDICTING HALLUCINATIONS

CROSS-REFERENCE TO RELATED APPLICATIONS

The present invention claims priority to the European patent application EP 16206649.2 that was filed on Dec. 23, 2016, the entire contents thereof being herewith incorporated by reference.

FIELD OF THE INVENTION

The invention relates to a robotic system and its use for predicting the probability of occurrence of hallucinations in a subject.

BACKGROUND ART

Hallucinations (sensory perceptions in the absence of any external stimulus) are severe and frequent symptoms, affecting an estimated three (3) million patients with Parkinson's disease and 30 million patients with schizophrenia worldwide and causing major health costs in Europe and the United States alone, respectively $23 billion and $120 billion per year. Despite increased efforts in neuroscience research, current understanding in neuroscience about hallucinations is still limited and diagnosis and therapy for hallucinations remains challenging. Strikingly, diagnosis of hallucinations still relies on subjective verbal descriptions of the patient and correct classification by the physician, differing from the symptoms of most medical conditions that are quantified based on biomedical markers.

Parkinson's disease (PD) is a chronic and progressive disorder of the central nervous system that primarily affects the motor system. More than 7 million people worldwide suffer from PD, and approximately 60,000 Americans are newly diagnosed with PD each year. PD is associated with an estimated direct and indirect health cost of nearly $23 billion per year in the United States and Europe alone, including treatment, social security payments, lost income from inability to work, and others.

Although in the early stages of the disease most of the major symptoms are related to the motor system (tremor, bradykinesia, muscle stiffness), the large majority of PD patients in later stages of the disease suffer from moderate to severe cognitive disturbances and/or hallucinations (Diederich et al., "Hallucinations in Parkinson disease," Nature Reviews Neurology, Vol. 5, Iss. 6, pp. 331-342, 2009). Motor symptoms are caused by loss of dopamine neurons in the substantia nigra and well-defined alterations in subcortical motor networks (Agid, Yves, "Parkinson's disease: pathophysiology," The Lancet 337, No. 8753, 1991, pp. 1321-1324). The cognitive disturbances and especially hallucinations in PD patients are less well investigated and their underlying brain mechanisms are currently unclear. This is unfortunate given their prominence in later phases of PD and their negative prognostic value.

Hallucinations, defined as sensory perceptions without any external stimulus, are an extremely common feature of PD, affecting approximately 50% of patients (Wood et al., "Fifty percent prevalence of extracampine hallucinations in Parkinson's disease patients," Frontiers in Neurology, Vol. 6, 2015, p. 263). As mentioned, the presence of hallucinations has been shown to be of negative prognostic value as they are associated with an increased risk of dementia, depression, and other cognitive deficits, nursing home placement, and death. One particular type of minor hallucination called the feeling of a presence (FoP) is defined as the sensation that somebody is nearby when no one is actually present. FoP is not only recognized as the most prevalent hallucination in PD, but also as a precursor of other types of major hallucinations, including psychotic symptoms and has recently been included in the new diagnostic criteria for PD-associated psychosis (Ravina et al., "Diagnostic criteria for psychosis in Parkinson's disease: report of an NINDS, NIMH work group," Movement Disorders Vol. 22, No. 8, 2007, pp. 1061-1068).

However, the detailed relations between FoP and major hallucinations remain uncertain. FoP is important for two main reasons: to reassure the patient that FoP is not uncommon in PD, and that they are not terrible hallucinations) and to have the physician realize that increasing PD medication may induce hallucinations and hence such symptoms are a warning. In current medical practice, despite the fact that hallucinations are key symptoms in PD, their clinical assessment is based upon semi-structured interviews between patient and physician and relies on the patient's verbal account and the physician's correct classification and diagnostic application. In a prospective analysis in incident, untreated PD patients, Pagonabarraga et al. characterized the FoP as a frequent and very early non-motor symptom that may even predate the onset of parkinsonian motor symptoms (Pagonabarraga et al., "Minor hallucinations occur in drug-naive Parkinson's disease patients, even from the premotor phase," Movement Disorders, Vol. 31, No. 1, 2016, pp. 45-52). In another study, Wood et al. outlined that the onset of visual hallucinations commonly precedes that of cognitive impairment in PD, pinpointing on the need of prospective natural history studies of extracampine hallucinations, including FoP), in PD patients without cognitive impairment, forecasting that visual hallucinations would be preceded by the occurrence of extracampine hallucinations. (Wood et al., "Fifty percent prevalence of extracampine hallucinations in Parkinson's disease patients," Frontiers in neurology, Vol. 6, Iss. 263, 2015, p. 1).

As it is evident, all these studies are statistical prospective studies, which are prone to errors due to the subjective interpretation of the physician, the possibly incorrect report of the patient and the criteria for exclusion/inclusion of a patient in the study.

This clearly differs from most symptoms in medicine, including the motor symptoms in PD, that can be quantified to e.g. guide diagnostics and the choice of the proper medical treatment. Accordingly, there are currently no biological markers for hallucinations in PD, or any other diseases with hallucinations, although such markers are needed to detect PD patients with hallucinations and other related consequences, such as dementia, home placement, depression, death, as early as possible to e.g. adapt medical treatments. Of note, such patient-physician interviews are almost never carried out while the patient actually suffers from hallucinations; hallucinations may have occurred days, weeks, or months earlier and therefore correct medical classification relies in addition on a patient's correct memory and verbal description of the hallucinations to the physician.

There are currently no medically accepted procedures allowing to induce the FoP or hallucinations in PD patients under safe and controlled conditions. This has limited basic neuroscience research to understand the brain mechanisms underlying hallucinations and also hindered the development of related diagnostic and therapeutic procedures that could replace, improve, or complement existing pharmacological treatments that have many serious medical side effects. Accordingly, in light of the above deficiencies of the background art, novel and substantially improved procedures and methods FOR predicting the likelihood of the occurrence of hallucinations are strongly desired.

SUMMARY

In order to find a solution to the limits of the background art for what concerns the systematic assessment of the impact that hallucinations may have in the PD, either for diagnosis, prognosis and/or adaptation/personalization of the pharmacological treatment of psychosis/hallucinations in affected subjects, the inventors developed a neurotechnological system and implemented methods for using thereof. Some aspects of the present invention is at least partially based on the disclosure of U.S. Pat. Pub. No. 2016/0176053, this reference herewith incorporated by reference in its entirety, describing a device for the induction of the feeling of a presence and its possible impact in schizophrenia patients.

In particular, the key technical challenge addressed by some of the aspects of the present invention was to develop a robotic system and an associated method able to quantitatively and qualitatively assess, via a rational analysis named by the inventors "hallucination stress test," the likelihood of a subject to experience major hallucinations. The device proved able to induce the FoP safely, repeatedly, and under highly controlled experimental conditions. In an experimental setting, it has been surprisingly observed that upon undergone to the hallucination stress test, patients with PD experienced the feeling of a presence when the master and the slave devices were timely mismatched with a particular delay, and that the delay strikingly differed from the delay wherein healthy, reference subjects experienced the same perception. View in its entirety, according to some aspects of the present invention, the previously-developed device is substantially improved by adapting it particularly to the investigation of patients with PD in order to ameliorate prognosis, and possibly diagnosis and therapy of major hallucinations in PD, and advances neuroscientific understanding of the FoP; moreover, the hallucination stress test seems to allow the identification and the characterization of a new "psycho-marker," both behavioural and neural in nature, with broad diagnostic, prognostic, and therapeutic impact, in particular for Parkinson's Disease patients.

Therefore, according to one aspect of the present invention, a method of predicting the likelihood of the occurrence of hallucinations in a subject is provided, the method preferably including the following steps:

(a) administering a spatially and/or temporally and/or force conflicting sensorimotor stimulation(s) in the subject through a master-slave robotic system by connecting the subject with at least one robotic master device so that the subject can move, move on or manipulate it, operably connecting the master device with a slave device, and make the subject move, move on or manipulate the at least one master device so that the subject is directly or indirectly touched by the slave device according with the master device's movement;

(b) recording the subjective response of the subject concerning the induction of the feeling of a presence (FoP) upon administration of the conflicting sensorimotor stimulation(s);

(c) recording data regarding the difference in time and/or space and/or force activation of the slave device in response to the activation of the master device associated with a subjective response of the subject; and (d) comparing the results of the recorded data with a set of reference sensorimotor stimulation(s) data.

Moreover, preferably a difference between the data recorded in steps (b) and (c) and the reference data is positively associated with the likelihood of the occurrence of hallucinations in a subject.

In one embodiment, the method further includes a step (c') of recording physical and/or physiological parameters associated with the subjective response recorded in step b).

In one embodiment, the physical and/or physiological parameters are obtained through imaging and/or measure of the activity of the subject's brain, for example measuring the electrical activity through electroencephalography, while the subject is operating the master-slave robotic system.

In one embodiment, the recorded data are correlated with other data derived from the subject or other subjects, the other data including behavioral data, data related to olfactory dysfunctions, genetic data, structural brain data, functional brain data or any combination of the foregoing.

In one embodiment, the reference sensorimotor stimulation(s) data are obtained from healthy subjects.

In one embodiment, the reference sensorimotor stimulation(s) data have been obtained from healthy subjects upon administration of a spatially and/or temporally and/or force conflicting sensorimotor stimulation(s) thereon.

In one embodiment, the subject has been diagnosed to have, or is affected by, Parkinson's Disease.

In one embodiment, the conflicting sensorimotor stimulation is a temporal mismatch between the master device activation and the slave device response.

In one embodiment, the conflicting sensorimotor stimulation(s) are modulated over time.

In one embodiment, the method further comprises the step of altering the visual and/or auditory perception of the surrounding environment of the subject, for example via at least one of blindfolding and hearing shielding.

In one embodiment, the master device is connected to a moving part of the subject, such as a limb or a limb extremity, and the slave device touches a non-limb body part of the subject.

Another aspect of the invention relates to a system. The system preferably includes:

(a) a master device adapted to be moved, moved on or manipulated by a subject;

(b) a slave device operably connected with the master device and adapted so that the subject is directly or indirectly touched by the slave device according with the master device's movement;

(c) a computer device operably connected to both the master and the slave device, the computer device configured to:

modulate the time and/or space and/or force activation of the slave device in response to the activation of the master device;

record data regarding the difference in time and/or space and/or force activation;

comparing the recorded data with reference data; and graphically or numerically showing the result of the comparison on a display means, for example a display screen of a computer.

In one embodiment, the computer device modulates the activation of the slave device over time.

In one embodiment, the computer device modulates the activation of the slave device so to create a temporal mismatch between the master device activation and the slave device response over time.

In one embodiment, the system further comprises means for imaging or measuring the activity of the subject's brain, for example an electroencephalography system.

In one embodiment, the master device and/or the slave device are wearable.

In one embodiment, a non-transitory computer readable medium is provided, the computer readable medium having computer instructions recorded thereon for performing a method when executed by a computer device having a processor that is in operative connection with a robot master device and a robotic slave device for interaction with the subject.

Still a further object of the present invention relates to the use of the described system for predicting the likelihood of the occurrence of hallucinations in a subject.

In one embodiment, the subject has been diagnosed to have, or is affected by, Parkinson's Disease.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1A:
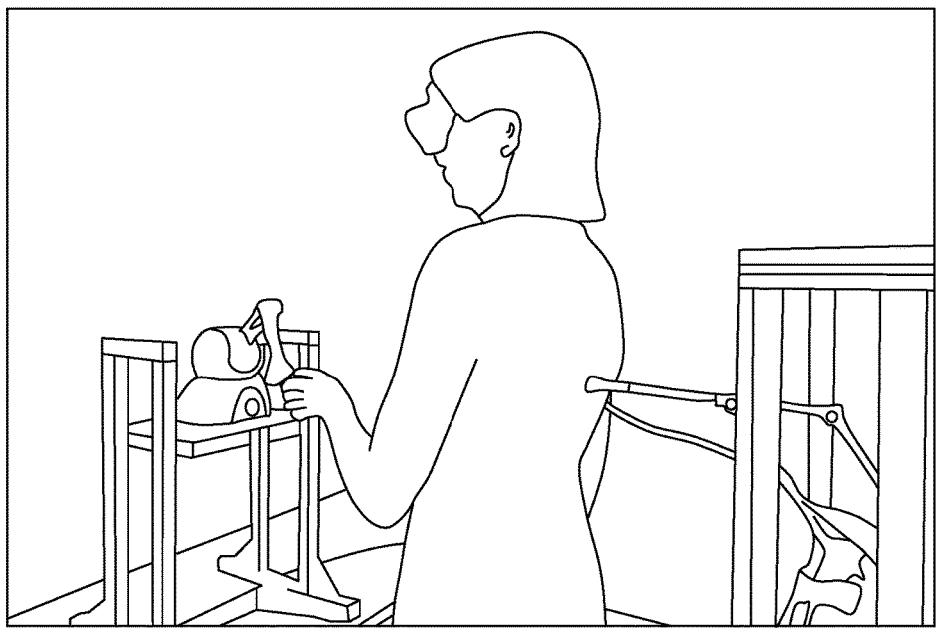
FIGS. 1A and 1B shows a background art embodiment of the master-slave device showing a user operating the device from a side-perspective view (FIG. 1A), and a top view (FIG. 1B)

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an", and "the" include plural referents unless the context clearly dictates otherwise. Thus, for example, reference to "a device" includes a plurality of such devices and reference to "a subject" includes reference to one or more subjects, and so forth.

Also, the use of "or" means "and/or" unless stated otherwise. Similarly, "comprise", "comprises", "comprising", "include", "includes", and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

As already outlined, the aim of the present invention, including both the developed method and the related system, was to identify the individual (and specific) parameters to induce the feeling of a presence in humans and to possibly classify populations of subjects for their susceptibility to experience major hallucinations in the future. The developed method combines a robotic system and subjective experiences, and in certain embodiments it is further supported by analysis of physical and/or physiological parameters associated with the subjective response recorded. For instance, the system can comprise means for imaging and/or measuring the brain activity of the tested subject by various type of devices, for example electroencephalography (EEG) device: the robotic system modulates this subjective experience(s) by introducing a sensorimotor conflict in the subject and the functional connectivity can be measured in real time, via for example EEG.

As it will be apparent, in the frame of the developed method, the FoP is not to be considered as a hallucination; on the contrary, it is rather an illusion, and particularly an illusion voluntarily and rationally induced. An "illusion" is a distortion of a sensorial perception, caused by the way the brain normally organizes and interprets the received information. Unlike a hallucination, which is a distortion in the absence of a stimulus, an illusion describes a misinterpretation of a true sensation, i.e. due to an external stimulus. In this context, it can be stated that the present invention is the first report of the use of an illusion to predict the likelihood of the occurrence of a pathological condition in humans, namely hallucinations, which has been corroborated by experimental evidences in human beings.

Accordingly, according to one aspect of the present invention, it has been shown and proved to induce specific altered states of bodily consciousness by manipulating sensorimotor inputs through a custom-made neurotechnological system that allows to apply a large range of well-controlled bodily stimulations. Aspects of this system have been shown in U.S. Patent Publication No. 2016/0176053, this reference herewith incorporated by reference by its entirety, but it has been modified and substantially improved herein to implement a system able to fit the need of the specific technical problem behind the predicting method.

Figure 1B:
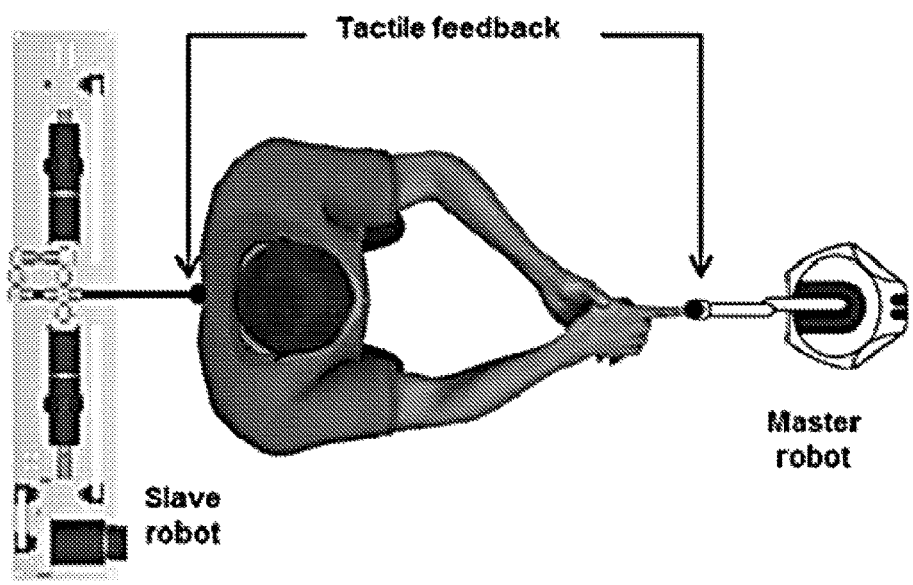
Figure 4:
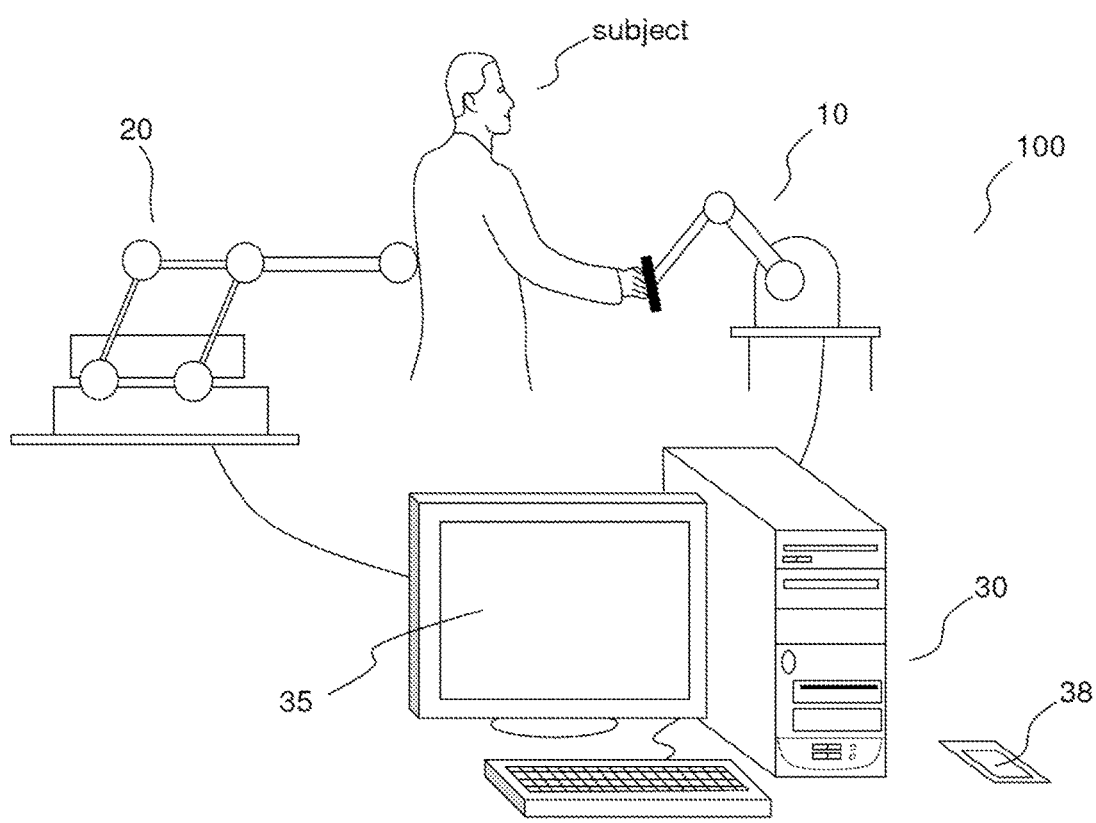
FIG. 4 shows a schematic perspective view of a system for operating the master-slave device, according to an aspect of the present invention.

As shown in FIG. 4, the master-slave robotic system 100 comprises a master device 10 (the "master") having unidirectional control over one or more other slave devices 20 (the "slave(s)"). Both devices are governed by software that is executed on a computer device 30, and they are operably connected among them in order to reproduce specific subject's induced movement and the related feedback. A subject S is connected with the robotic master device 10 so that (s)he can move, move on or manipulate it. When the subject moves, moves on or manipulates the master device 10 through moving parts of his/her body, preferably through limbs or extremities, in the variant shown his hand, (s)he is directly or indirectly touched by the slave device 20 according with a movement of master device 10 movement, preferably in a non-limb part of the body such as for instance the trunk. The term "according" means in a proper or appropriate way, i.e. in a way that suits the facts, needs, or requirements of a situation. The movement of the slave device 20 can perfectly mirror the movement of the master device 10 both in terms of spatial and temporal coordinates, or those movements can be performed in e.g. an asynchronous and/or asymmetric fashion. The mismatch (temporal and/or spatial and/or force mismatch) introduced by the robotic system is such that the subject receives spatially and/or temporally and/or force conflicting sensorimotor stimulation(s) up to a "break point" of sensory alteration in which the illusion is reached. One embodiment of the robotic system 100 is composed of a commercial master haptic interface, the Phantom Omni (SensAble Technologies), and a three degree-of-freedom (DOF) slave robot, as shown in the background art of FIGS. 1A and 1B.

In an implemented embodiment, a temporal mismatch is introduced by the robotic system, that is, the conflicting sensorimotor stimulation is given by an asynchronous response of the slave device 20 compared to the activation of the master device 10 driven by the operating subject, so that the subject is touched by the slave device with a short delay, usually between 50 ms and 500 ms, compared to the induced movement of the master device. It has been in fact shown in the past by the present inventors that during an asynchronous stimulation, i.e. a stimulation by which the touch on the subject's body provided by the slave device is temporary delayed vis-à-vis the corresponding master device's movement, a subject is able to experience a FoP. However, the present method is not limited to temporal mismatches, and can be envisaged to induce force and/or spatial mismatches, alone or in combination to a temporal mismatch.

According to one aspect of the present invention, the robotic system is operably connected with a computer device 30 executing a computer program, the computer program comprising instructions to modulate the time and/or space and/or force activation of the slave device in response to the activation of the master device, to record data regarding the difference in time and/or space and/or force activation, to compare the recorded data with reference data; and to graphically or numerically, or otherwise display information with a display device 35, to show the result of the comparison on a display device 35, as an indicator of the likelihood of the occurrence of hallucinations in a subject. Also, according to one aspect of the present invention, a non-transitory computer readable medium 38 is provided, the computer readable medium 38 having computer instructions recorded thereon for performing a method when executed by a computer device 30 having a processor that is in operative connection with a robot master device 10 and a robotic slave device 20 for interaction with the subject S.

One goal of the device, system, and method is to record data concerning the difference in time and/or space and/or force activation of the slave device in response to the activation of the master device, such as for example the temporal mismatch in terms of master device activation/slave device response delay, and compare the results of the recorded data with a set of reference data. The data can be a set of reference sensorimotor and can have been obtained from healthy subjects upon administration of a spatially and/or temporally and/or force conflicting sensorimotor stimulation(s) thereon. As will be detailed below, in case a difference between the recorded data and the reference data is found, this is positively associated with the likelihood of the occurrence of hallucinations in a subject. The recorded data can be in some embodiments further correlated with other data derived from the subject or other subjects, the other data comprising behavioral data, data related to olfactory dysfunctions, genetic data, structural brain data, functional brain data or any combination of the foregoing.

Preferably, the conflicting stimulation, such as the above-described temporal mismatch, master device activation/slave device response delay, is modulated (e.g., increased) gradually or sharply over time by the computer device till the so-called "break point." Once the break point is reached, specific mismatches can be associated to it, allowing to generate different sub-populations, according to those parameters. In an exemplary, implemented embodiment of the hallucination stress test, for each specific temporal mismatch, for example a delay between the master and the slave, a subject is asked to perform a certain number of touches, i.e. moving the master device in front and receiving touch on the back by the slave device, such as between five (5) to ten (10) touches, after which is asked to report whether he had the feeling of a presence. This can be done by a forced-choice task: "did you feel somebody behind you, touching you?" This is reported in a graph as proportion, or probability, of reporting a FoP for a given specific delay over a certain number of trials/repetitions for delay.

Figure 2:
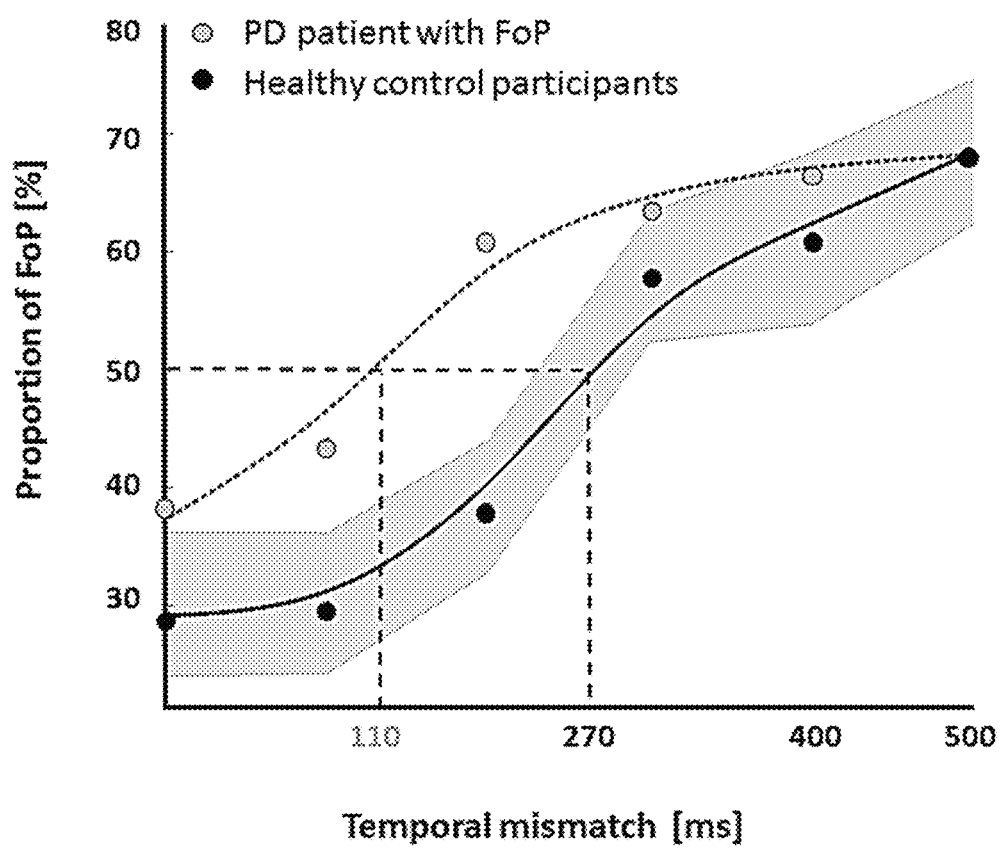
FIG. 2 shows a graph representing the hallucination stress test. Light grey line and dotted line curves indicates pathological response to the hallucination stress test, while the black line curve represents the response of healthy subjects undergone to the same conflicting sensorimotor stimulation.

What has been surprisingly reported in this experimental setting, and shown in FIG. 2, was that, when plotting on a graph the data regarding the probability of experiencing a FoP as a function of the used delay, the curve of a test Parkinson's Disease patient, experiencing the feeling of a presence in some instances of his daily life, had a strikingly different profile compared to data obtained by reference, healthy volunteers. In the graph shown in FIG. 2, the dotted curve shows the real data obtained from a Parkinson's Disease patient who experienced the feeling of a presence, while the solid curve is the reference response curve obtained from healthy volunteers upon induction of conflicting sensorimotor stimulations and the related time mismatches. In this scenario it has been assessed that, the probability of experiencing a FoP being equal, a Parkinson's Disease patient experiences FoPs with a master activation/slave response delay which is hugely lower compared to healthy volunteers. In the test reported in FIG. 2, a 110 ms delay for a Parkinson's Disease patient compared to 270 ms for healthy volunteers is shown, as a mean or average value. Moreover, it has being surprisingly reported that for the "test" subject affected by Parkinson's Disease, not only a FoP experience was reported, but the presence felt was reported in a lateral position compared to the subject; on the contrary, healthy subjects reported the feeling of a presence behind them. This further difference could be an important parameter in discriminating populations of subjects reporting, upon the hallucination stress test, the FoP, in order for instance to provide an early identification of healthy or recently-diagnosed PD subjects having a higher probability to experience hallucinations in the future, or even possibly an early identification of Parkinson's Disease itself as well as further psychotic disorders.

Accordingly, because the background art studies the FoP has been positively associated with the likelihood of Parkinson's Disease patients to experiencing major hallucinations during the development of the disease, the present method and the associated system are deemed to be a reliable tool for predicting the likelihood of occurrence of hallucinations in a subject, particularly those subjects who have been diagnosed to have the disease, or are actually affected by the same. The device can be thus used also for prognosis, for example to differentiate the risk for Parkinson's Disease patients to develop dementia, depression or the risk of death, and to possibly tune the pharmacological treatment used to treat psychosis-like symptoms in Parkinson's Disease.

As will be evident for a person skilled in the art, miniaturized versions of the slave device can be imagined, as well as wearable or even body implantable slave devices for more tailored and precise control thereof. For instance, ad hoc clothes such as pants, jackets, helmets, hats and the like can be imagined, including miniaturized versions of the slave device therein, to be worn in situations when a FoP is required or desired. The same is also true for the master device, which can be embodied as a wired glove (also known as "dataglove" or "cyberglove"), i.e. an input device for human-computer interaction worn like a glove, but even sophisticated exoskeleton limbs or the like.

In certain embodiments, some aspects already disclosed in U.S. Patent Publication No. 2016/0176053, the method further includes the step of altering the visual and/or auditory perception of the surrounding environment of the subject, for example via blindfolding or hearing shielding. The exclusion of associated senses in the experimental setting can facilitate the implementation of the illusion due to the ease of inducing a "cerebral short-cut" between what is performed, i.e. the master device movement, and what is perceived, i.e. the slave device touch, without being biased by e.g. what is seen during the experiment.

In some embodiments of the invention, the system further comprises means for imaging or measuring the activity of the subject's brain, for example an electroencephalography or functional magnetic resonance imaging (fMRI) system, operably connected with the master/slave robotic system. Accordingly, the method can be adapted to further comprise the step of imaging and/or measuring the activity of the subject's brain, for example measuring the electrical activity through electroencephalography, while the subject is operating the master-slave robotic system. In a prophetic example, the inventors will perform two neuroimaging studies, using a recently finalized fully MRI (Magnetic Resonance Imaging) compatible version of the robotic system and even an EEG (Electroencephalogram)-adapted versions thereof in combination with brain imaging techniques (fMRI and high-density EEG) in PD patients and healthy age-matched controls. The hallucination stress test could therefore allow to base the likelihood of experiencing hallucinations in PD, not only on the basis of an interview with patients concerning their past hallucinations, but also on their objective responses to the hallucination stress test and its association to other relevant behavioural, brain and genetic data.

Furthermore, the developed system and the associated method for using thereof could be additionally used to inform diagnosis (determination of the nature of the hallucination) and prognosis (the forecast of the probable course and outcome of hallucinations) of patients with PD.

Further studies will be performed in order to confirm the results obtained on the PD patient with FoP vs healthy controls previously described. In particular, it will be investigated which temporal delay maximizes the FoP, how increasing temporal delays, and thereby increasing level of "sensorimotor stress," affect the chances of reporting the FoP (i.e. FoP temporal sensitivity), and the sensation of passivity, for example loss of agency, or other alterations of bodily experience, for example illusory self-touch, and how these parameters differ between PD patients and age-matched control groups.

To aid prognosis, in a further prophetic example, it is planned to investigate three different PD patient populations in three separate studies evaluating the prognostic potential of the robotic system and the hallucination stress test. In one study it will be investigated whether the hallucination stress test dissociates PD patients with hallucinations (requiring treatment adaptations) from those PD patients without hallucinations; for this, responses in the hallucination stress test in PD patients who only have hallucinations consisting of FoP will be compared to those with FoP as well as other hallucinations.

In another study, it will be investigated the responses in the hallucination stress test in PD patients with mild dementia versus PD patients with no dementia, predicting that PD patients with dementia have higher sensitivity to the device-induced FoP than PD patients without dementia.

Figure 3:
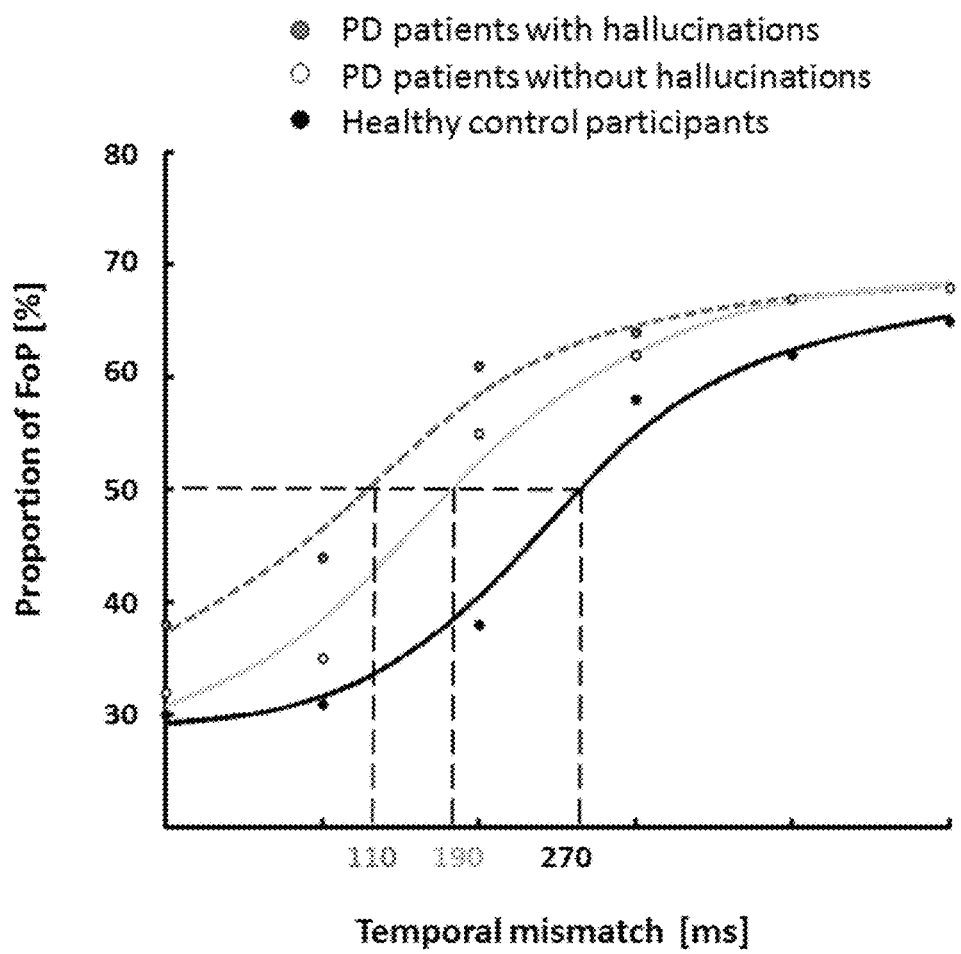
FIG. 3 shows a graph as an example of predicted results to the hallucination stress test for two different patient populations.

Finally, responses in the hallucination stress test in PD patients with depression versus PD patients with no dementia will be studied, predicting higher sensitivity to the device-induced FoP in PD patients with depression. For example, see the results in FIG. 3, example of predicted results for two different patient populations.

In separate brain imaging studies, behavioural responses of the evoked brain activations during the hallucination stress test will be studied.

Moreover, Baker et al. has shown that dopaminergic drugs are associated with the induction or exacerbation of hallucinations in PD. See Baker et al., "Dopamine agonists in the treatment of early Parkinson's disease: a meta-analysis," Parkinsonism & Related Disorders, Vol. 15, No. 4, 2009, pp. 287-294. According to an aspect of the present invention, it has been shown that the present system and method is able to induce hallucinations when the associated method is performed, it is proposed to combine both approaches. To this aim, investigations on two different PD patient populations in two separate studies will be done, in order to evaluate whether PD receiving dopaminergic pharmacological treatments respond differently to the hallucination stress test.

In one study, it will be investigate whether the hallucination stress test dissociates PD patients who receive a high mean daily levodopa dose from PD patients who receive a low mean daily levodopa dose. Both patient groups will have hallucinations and it is predicted the former group will be more sensitive to the hallucination stress test. In another study the inventors will investigate responses in the hallucination stress test in PD patients receiving a dopaminergic agonist versus PD patients without dopaminergic agonist, predicting that PD patients receiving a dopaminergic agonist will have higher sensitivity to the device-induced FoP than PD patients without such treatments. Comparisons across both studies will be also performed, comparing device-induced hallucinations in PD patients with dopaminergic agonists versus PD patients with levodopa. In the longer-term these studies will help tailor and/or avoid the application of hallucination-inducing doses of standard pharmacological PD treatments.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A method of predicting a likelihood of an occurrence of hallucinations in a subject, the method comprising the steps of:
    administering at least one of a spatially, temporally, and force conflicting sensorimotor stimulation to the subject through a master-slave robotic system by connecting the subject with a robotic master device such that the subject can move, move on, or manipulate the master device;
    operatively connecting the master device with a slave device, and make the subject move, move on or manipulate the master device such that the subject is directly or indirectly touched by the slave device according to a movement of the master device;
    recording a subjective response of the subject with respect of an induction of a feeling of a presence (FoP) upon administration of a conflicting sensorimotor stimulation;
    recording data of a difference in at least one of a time, space, and force activation of the slave device in response to an activation of the master device associated with the subjective response of the subject; and
    comparing results of the recorded data with a set of reference sensorimotor stimulation data,
    wherein a difference between the recorded data and the set of reference sensorimotor stimulation data is positively associated with the likelihood of the occurrence of hallucinations in the subject, and
    wherein the subject has been diagnosed to have, or is affected by, Parkinson's Disease.

2. The method of claim 1, further comprising the step of:
    recording at least one of physical and physiological parameters associated with the recorded subjective response.

3. The method of claim 2, wherein the at least one of physical and physiological parameters are obtained through at least one of imaging and a measure of an activity of a brain of the subject.

4. The method of claim 3, wherein the at least one of physical and physiological parameters are obtained by measuring an electrical activity through electroencephalography while the subject is operating the master-slave robotic system.

5. The method of claim 1, wherein the recorded data are correlated with other data derived from the subject or other subjects, the other data including at least one of behavioural data, data related to olfactory dysfunctions, genetic data, structural brain data, and functional brain data.

6. The method of claim 1, further comprising the step of:
    obtaining the reference sensorimotor stimulation data from healthy subjects.

7. The method of claim 1, wherein the reference sensorimotor stimulation data have been obtained from healthy subjects upon administration of at least one of a spatially, temporally, and force conflicting sensorimotor stimulation thereon.

8. The method of claim 1, wherein the conflicting sensorimotor stimulation is a temporal mismatch between the master device activation and the slave device response.

9. The method of claim 1, wherein the conflicting sensorimotor stimulation are modulated over time.

10. The method of claim 1, further comprising the step of:
    altering at least one of a visual and auditory perception of a surrounding environment of the subject.

11. The method of claim 1, wherein the master device is connected to a moving body part of the subject, and the slave device touches a non-limb body part of the subject.

12. A system for predicting a likelihood of an occurrence of hallucinations in a subject comprising:
    master device configured to be at least one of moved, moved on, and manipulated by a subject;
    a slave device operably connected with the master device and adapted so that the subject is directly or indirectly touched by the slave device according with the master device's movement; and
    a computer device operably connected to both the master and the slave device, the computer device configured to modulate at least one of a time, space, and force activation of the slave device in response to an activation of the master device;
        record data regarding a difference in at least one of time, space and force activation;
        compare the recorded data with reference data; and
        graphically or numerically showing a result of the comparison on a display device, as an indicator of the likelihood of the occurrence of hallucinations in a subject,
    wherein the subject has been diagnosed to have, or is affected by, Parkinson's Disease.

13. The system of claim 12, wherein the computer device modulates the activation of the slave device over time.

14. The system of claim 12, wherein the computer device modulates the activation of the slave device so to create a temporal mismatch between the master device activation and the slave device response over time.

15. The system of claim 12, further comprising:
    a device for imaging or measuring the activity of the subject's brain.

16. The system of claim 12, wherein at least one of the master device and the slave device is wearable.

17. The system of claim 12, wherein the computer device is configured to predict the likelihood of the occurrence of hallucinations in the subject.

18. A method of diagnosing an actual or future affection of a subject by Parkinson's Disease comprising the steps of:
    administering at least one of a spatially, temporally, and force conflicting sensorimotor stimulation to the subject through a master-slave robotic system by connecting the subject with a master device such that the subject can move, move on, or manipulate the master device;
    operatively connecting the master device with a slave device, and make the subject move, move on or manipulate the master device such that the subject is directly or indirectly touched by the slave device according to a movement of the master device;
    recording a subjective response of the subject with respect of an induction of a feeling of a presence (FoP) upon administration of a conflicting sensorimotor stimulation;
    recording data of a difference in at least one of a time, space, and force activation of the slave device in response to an activation of the master device associated with the subjective response of the subject; and
    comparing results of the recorded data with a set of reference sensorimotor stimulation data, a difference between the recorded data and the set of reference sensorimotor stimulation data being positively associated with an actual or future affection of the subject by Parkinson's Disease.

19. The method of claim 18, wherein the difference between the recorded data and the set of reference sensorimotor stimulation data shows a lower time delay that is positively associated with the actual or the future affection by Parkinson's Disease.

20. A system for providing a diagnostic indication of an actual or future affection by Parkinson's Disease in a subject comprising:

master device configured to be at least one of moved, moved on, and manipulated by a subject;

a slave device operably connected with the master device and configured to directly or indirectly touch the subject according with a movement of the master device; and a computer device operably connected to both the master and the slave device, the computer device configured to modulate at least one of a time, space, and force activation of the slave device in response to an activation of the master device;

record data regarding a difference in at least one of time, space and force activation;

compare the recorded data with reference data; and graphically or numerically showing a result of the comparison on a display device, the result of the comparison serving as a diagnostic indication of an actual or future affection of the subject by Parkinson's Disease.

21. The system of claim 20, wherein the result of the comparison shows a lower time delay positively associated with the actual or the future affection by Parkinson's Disease.

\* \* \* \* \*